United States Patent [19]

Hohnjec et al.

[11] 4,187,244
[45] Feb. 5, 1980

[54] PROCESS FOR THE RESOLUTION OF RACEMIC ALPHA-AMINONITRILES

[75] Inventors: Marijan Hohnjec, Zagreb; Miha Japelj, Novo mesto, both of Yugoslavia

[73] Assignee: KRKA, Farmaceutika, Kemija, Kozmetika, zdravilisca in gostinstuo, Novo mesto, n.sd.o., Novo Mesto, Yugoslavia

[21] Appl. No.: 891,973

[22] Filed: Mar. 30, 1978

[30] Foreign Application Priority Data

Apr. 8, 1977 [YU] Yugoslavia .............................. 937/77

[51] Int. Cl.² ............................................ C07C 121/66
[52] U.S. Cl. .............................. 260/465 E; 260/465 D
[58] Field of Search ........................ 260/465 D, 465 E

[56] References Cited

U.S. PATENT DOCUMENTS

| 2,906,772 | 9/1959 | Weijlard | 260/465 E |
| 3,344,023 | 9/1967 | Reinhold et al. | 260/465 E X |
| 3,721,697 | 3/1973 | Reinhold et al. | 260/465 E X |

OTHER PUBLICATIONS

Stein et al., J.A.C.S., 77 (1955), pp. 700–703.

*Primary Examiner*—Joseph Paul Brust
*Attorney, Agent, or Firm*—Pollock, Vande Sande & Priddy

[57] ABSTRACT

Process for the resolution of certain racemic α-aminonitriles into optically active enantiomers which includes treating the racemic α-aminonitriles with (−)-mandelic acid in an alkanol/$C_{5-8}$ hydrocarbon mixture to obtain a racemic mixture of diastereoisomeric D and L salts of (−)-mandelic acid, macerating the salts with an alkanol/$C_{5-8}$ hydrocarbon mixture; neutralizing the L-form; extracting the neutralized product; and converting it into a stable form.

16 Claims, No Drawings

PROCESS FOR THE RESOLUTION OF RACEMIC ALPHA-AMINONITRILES

The present invention relates to a process for the resolution of racemic alpha-aminonitriles of the general formula

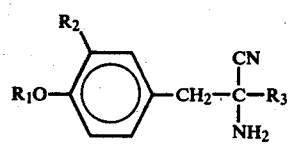

wherein
$R_1$ stands for a hydrogen atom or a methyl group,
$R_2$ stands for a hydrogen atom or a methoxy group, and
$R_3$ stands for a hydrogen atom or a methyl group, into optically active enantiomers.

The resolution of racemic alpha-aminonitriles into the corresponding optically active enantiomers is the most important and economically rational step in the synthesis of optically active alpha-amino acids, especially in the synthesis of p-hydroxy-phenyl glycine, 3,4-dihydroxy-phenyl glycine, 3,4-dihydroxy-phenyl alanine (DOPA) and alpha-menthyl-3,4-dihydroxy-phenyl alanine (methyl DOPA), which are important intermediates in pharmaceutical chemistry (Synthesis of methyl DOPA: G. Stein, H.A. Bronner and K. Pfister, J.Am. Chem. Soc. 77, 700 (1955); Antihypertensive activity of methyl DOPA: A. Sjoerdsma and S. Udenfriend, Biochem.Pharmacol. 8, 164 (1961)).

In the manufacture of optically active alpha-amino acids, the process comprising a preliminary resolution of the corresponding racemic alpha-aminonitriles and further chemical conversions of the isolated diastereoisomeric salts into the corresponding optically active alpha-amino acids offers a distinct economical and technological advantage over the process, wherein there is performed the resolution of the racemic alpha-amino acids into the corresponding optically active alpha-amino acids, especially as the other (inactive) diastereoisomer of the corresponding alpha-aminonitrile may be rationally utilized and by means of racemization in alkaline media again converted into the corresponding D,L-aminonitrile. The racemization of the undesired optically active enantiomer of the corresponding alpha-amino acid is not feasible, which means that such a process offers substantially lower yields in the whole synthesis and is technologically inferior in comparison to the process based on preliminary resolution of the racemic aminonitriles.

It has now been found that in accordance with the present inventive process the racemic alpha-aminonitriles may be resolved in a technologically advantageous manner into the corresponding optically active enantiomers as follows:

Alpha-aminonitriles are treated with (−)-mandelic acid in the system alkanol/$C_{5-8}$-hydrocarbon in order to obtain a racemic mixture of diastereoisomeric D and L salts of (−)-mandelic acid, which is macerated with an alkanol/ $C_{5-8}$-hydrocarbon mixture, to yield a salt of D- and L-aminonitrile respectively with (−)-mandelic acid, the L-form is neutralized and the obtained product is extracted with a suitable chlorinated aliphatic hydrocarbon, whereupon it is converted into a stable form like a hydrochloride or an acyl derivative.

The salt of D-aminonitrile with (−)-mandelic acid is racemized by means of ammonia and recycled.

The resolution of racemic aminonitriles in organic solvents in accordance with the invention represents in every respect a technological advantage over the resolution of D,L-aminonitriles by means of other optically active reactants in aqueous media, especially as said organic solvents may be regenerated in a simple manner.

As preferred medium for the reaction with (−)-mandelic acid and the maceration there is used an ethanol/petroleum ether mixture. The temperature during the reaction with (−)-mandelic acid should be within the range of 0° to −10° C., whereas the maceration temperature should be within the range of +15° to +30° C.

The maceration of the obtained precipitated racemic salt by means of an alkanol/$C_{5-8}$-hydrocarbon causes the dissolving of the corresponding diastereoisomeric salt of (−)-mandelic acid with L-aminonitrile, whereas the D-aminonitrile salt remains in the crystalline form. The neutralization of the L-salt by means of ammonia, followed by an extraction with chloroform and a final precipitation with hydrochloric acid yields the corresponding L-(+)-aminonitrile.hydrochloride.monohydrate of the general formula

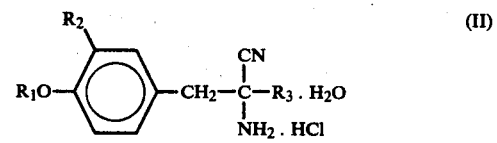

wherein $R_1$, $R_2$, $R_3$ have the meanings defined in the general formula I.

L-aminonitrile may be isolated also in the form of more stable L-acyl-aminonitriles of the general formula

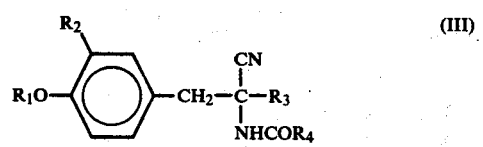

wherein $R_1$, $R_2$, $R_3$ have the meanings already defined in the general formula I, whereas $R_4$ stands for an alkyl group comprising 1 to 5 carbon atoms.

L-acyl-aminonitriles are obtained by the reactions of the corresponding L-aminonitriles with acid anhydrides, preferably with acetic anhydride, in chlorinated aliphatic hydrocarbons, preferably in chloroform.

the insoluble salt of (−)-mandelic acid with D-aminonitrile is racemized by means of an aqueous ammonia solution and the regenerated D,L-aminonitrile is recycled.

The hydrolysis of the corresponding L-aminonitrile.-hydrochloride.monohydrate and L-acetylamino-nitrile may yield the L form of the amino acids.

The inventive process is more closely illustrated, yet in no way limited by the following Examples.

EXAMPLE 1

17.6 g. (0.08 mole) of D,L-amino-(3,4-dimethoxy-benzyl)-propionitrile (D,L-aminonitrile) and 12.5 g. (0.082 mole) of (−)-mandelic acid are dissolved in 100 mls. of ethanol, subsequently there are added 200 mls. of petroleum ether and heated under reflux for 5 minutes. The solution is filtered and the filtrate is cooled under stirring to −5° C. The stirring is kept on for further 3 hours at this temperature, whereupon the precipitate is filtered and washed with two 20 mls. portions of petroleum ether. There are obtained 25.45 g. (86 %) of a mixture of diastereoisomeric salts, $[\alpha]_D^{20} = -61.65°$ (c=2, methanol). The salt thus obtained is macerated in 300 mls. of a petroleum ether/ethanol mixture (2:1) for 4 hours at 23° C.

The precipitate is filtered off and there are obtained 13 g. (43.7 %) of the salt of (−)-mandelic acid with D-aminonitrile, $[\alpha]_D^{20} = -66.35°$ (c=2, methanol). To the filtrate containing the dissolved salt of (−)-mandelic acid with L-aminonitrile, there are added 100 mls. of petroleum ether, whereupon there is cooled to −5° C. and stirred at this temperature for 2 hours. The separated diastereoisomeric salt is filtered off and suspended in 100 mls. of water, subsequently there are added 25 mls. of chloroform, there is cooled to 0° to 5° C. and pH is adjusted to 6.9 by means of 6 N ammonia. The layers are separated and the aqueous layer is extracted with two 5 mls. portions of chloroform. The chloroform solution is added drop by drop to 20 mls. of cooled 6 N hydrochloric acid at 0° to 5° C. during 10 minutes. The reaction suspension is stirred at this temperature for 2 hours and filtered. The precipitate is washed with 10 mls. of cooled chloroform and dried. There are obtained 7.7 g. (35%) of L-(+)-aminonitrile. hydrochloride.monohydrate, $]\alpha]_D^{20} = +10.5°$ (c=2, methanol).

EXAMPLE 2

13 g. of the salt of D-aminonitrile with (−)-mandelic acid are suspended in 20 mls. of 12 N ammonia and heated for 30 minutes at 50° C. There is cooled to 0° C. and stirred at this temperature for 1 hour. the precipitate is filtered and washed with two 10 mls. portions of water. There are obtained 7.4 g. (42% theor.) of D,L-aminonitrile, m.p. 84 to 86° C.

EXAMPLE 3

In the same manner as in Example 1, the L-aminonitrile in chloroform solution is obtained from 25.45 g. of the diastereoisomeric salt mixture. To this solution there are added 10 mls. of acetic anhydride and the chloroform is distilled off. The reaction solution is heated for 5 minutes at 100° C. and cooled during 30 minutes to 10° C. The separated crystals of L-acetylaminonitrile are filtered off and washed with two 5 mls. portions of isopropanol. There are obtained 7.15 g. (34% theor.) of the product, m.p. 138 to 141° C. and $[\alpha]_D^{20} = -30.2$ (c=2, methanol).

What we claim is:

1. Process for the resolution of racemic α-aminonitriles of the general formula:

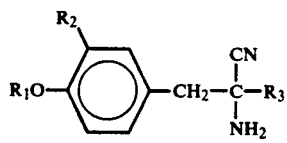

(I)

wherein $R_1$ stands for a hydrogen atom or a methyl group,
$R_2$ stands for a hydrogen atom or a methoxy group, and
$R_3$ stands for a hydrogen atom or a methyl group, into optically active enantiomers, which comprises:
(A) treating said recemic α-aminonitriles with (−)-mandelic acid in an alkanol/$C_{5-8}$ hydrocarbon mixture in order to thereby obtain a racemic mixture of diastereoisomeric D and L salts of (−)-mandelic acid;
(B) macerating said racemic mixture of diastereoisomeric D and L salts of (−)-mandelic acid with an alkanol/$C_{5-8}$ hydrocarbon mixture to thereby obtain a salt of D- and L-aminonitrile respectively with (−)-mandelic acid;
(C) neutralizing the L-form;
(D) extracting the neutralized product obtained in step (C) above with a chlorinated aliphatic hydrocarbon; and
(E) converting said neutralized product to a hydrochloride or acetyl derivative.

2. Process as claimed in claim 1, characterized in that salt of D-aminonitrile with (−)-mandelic acid is racemized by means of ammonia and recycled.

3. Process as claimed in claim 1, characterized in that the reaction with (−)-mandelic acid is performed at 0° to −10° C.

4. Process as claimed in claim 1, characterized in that the macerization is performed at a temperature of +15° to +30° C.

5. The process of claim 1 wherein the ratio of alkanol:$C_{5-8}$ hydrocarbon of the alkanol/$C_{5-8}$ hydrocarbon mixture employed in steps (A) and (B) is 1:2.

6. The process of claim 5 wherein said alkanol is ethanol and said $C_{5-8}$ hydrocarbon is petroleum ether.

7. The process of claim 1 wherein said alkanol is ethanol and said $C_{5-8}$ hydrocarbon is petroleum ether.

8. The process of claim 1 wherein said L-form is neutralized with ammonia.

9. The process of claim 1 wherein said chlorinated aliphatic hydrocarbon is chloroform.

10. The process of claim 3 wherein the macerization is performed at a temperature of +15° to +30° C.

11. The process of claim 1 wherein the ratio of alkanol:$C_{5-8}$ hydrocarbon of the alkanol/$C_{5-8}$ hydrocarbon mixture employed in steps (A) and (B) is 1:2; said alkanol is ethanol; said $C_{5-8}$ hydrocarbon is petroleum ether; said chlorinated aliphatic hydrocarbon is chloroform; said stable form is a hydrochloride or acyl derivative; the reaction with (−)-mandelic acid is performed at 0° to −10° C.; and the macerization is performed at a temperature of +15° to +30° C.

12. The process of claim 11 wherein said L-form is neutralized with ammonia.

13. The process of claim 11 wherein said L-form is neutralized with ammonia.

14. The process of claim 1 wherein the racemic α-aminonitrile is D,L-amino-(3,4-dimethoxy-benzyl)-propionitrile.

15. The process of claim 1 wherein the salt of D-aminonitrile with (−)-mandelic acid is racemized in alkaline media into the corresponding D,L-aminonitrile and recycled to the process.

16. The process of claim 11 wherein the salt of D-aminonitrile with (−)-mandelic acid is racemized in alkaline media into the corresponding D,L-aminonitrile and recycled to the process.

* * * * *